US012642884B1

(12) United States Patent
Magometschnigg et al.

(10) Patent No.: US 12,642,884 B1
(45) Date of Patent: Jun. 2, 2026

(54) SCLEROTHERAPY OF VENOUS BLOOD VESSELS

(71) Applicant: Croma-Pharma GmbH, Leobendorf (AT)

(72) Inventors: Heinrich Magometschnigg, Salzburg (AT); Michaela Magometschnigg, Salzburg (AT)

(73) Assignee: CROMA-PHARMA GMBH, Leobendorf (AT)

( * ) Notice: Subject to any disclaimer, the term of this patent is extended or adjusted under 35 U.S.C. 154(b) by 0 days.

(21) Appl. No.: 19/087,272

(22) Filed: Mar. 21, 2025

(30) Foreign Application Priority Data

Mar. 6, 2025 (EP) ..................................... 25162109

(51) Int. Cl.
| | |
|---|---|
| *A61L 24/08* | (2006.01) |
| *A61K 9/00* | (2006.01) |
| *A61L 24/00* | (2006.01) |
| *A61P 9/14* | (2006.01) |

(52) U.S. Cl.
CPC ............ *A61L 24/08* (2013.01); *A61K 9/0019* (2013.01); *A61L 24/0015* (2013.01); *A61P 9/14* (2018.01); *A61L 2430/36* (2013.01)

(58) Field of Classification Search
CPC .. A61L 24/08; A61L 24/0015; A61L 2430/36; A61K 9/0019; A61P 9/14
See application file for complete search history.

(56) References Cited

U.S. PATENT DOCUMENTS 3,982,017 A     9/1976  Thiele

FOREIGN PATENT DOCUMENTS

| BR | 102019008196 A2 | * | 11/2020 |
|---|---|---|---|
| GB | 2369996 A | | 6/2022 |

OTHER PUBLICATIONS

P. Ouvry et al., "Efficacy of Polidocanol Foam versus Liquid in Sclerotherapy of the Great Saphenous Vein: A Multicentre Randomised Controlled Trial with a 2-year Follow-up," Eur. J. Vasc Endovasc Surg. 2008, vol. 36, pp. 366-370.

Bai et al., "A Review of Sclerosing Foam Stability in the Treatment of Varicose Veins", Dermatologic Surgery, vol. 46, No. 2, Sep. 2019, pp. 10.

Breu et al., "Duplex ultrasound and efficacy criteria in foam sclerotherapy from the 2nd European Consensus Meeting on Foam Sclerotherapy 2006", Tegernsee, Germany, vol. 37, No. 1, Feb. 2008, pp. 90-95.

Castillo-Santaella et al., "Effect of Hyaluronic Acid and Pluronic-F68 on the Surface Properties of Foam as a Delivery System for Polidocanol in Sclerotherapy", Pharmaceutics, vol. 12, 1039, Oct. 30, 2020, pp. 1-16.

(Continued)

*Primary Examiner* — Carlos A Azpuru

(74) *Attorney, Agent, or Firm* — Workman Nydegger

(57) ABSTRACT

Sclerosing agent for use in treating a varicose, reticular or spider vein, wherein the sclerosing agent is administered in a formulation further comprising a water-soluble cellulose derivative, pharmaceutical composition comprising a sclerosing agent and a water-soluble cellulose derivative as well as a kit or a method for producing a foam comprising a sclerosing agent and a water-soluble cellulose derivative.

9 Claims, 3 Drawing Sheets

(56)  References Cited

OTHER PUBLICATIONS

Eckmann et al., "Polidocanol for Endovenous Microfoam Sclerosant Therapy", Expert Opin Investig Drugs. Dec. 2009, vol. 18, No. 12, pp. 1919-1927.
Nastasa et al., "Properties of polidocanol foam in view of its use in sclerotherapy", International Journal of Pharmaceutics, vol. 478, 2015, pp. 588-596.
Whiteley et al., "Modified Tessari Tourbillon technique for making foam sclerotherapy with silicone-free syringes", Phlebology, vol. 30, No. 9, 2014, pp. 1-4.

* cited by examiner

A

B

A

B

SCLEROTHERAPY OF VENOUS BLOOD VESSELS

The present invention relates to a sclerosing agent for use in treating a varicose, reticular or spider vein.

BACKGROUND OF THE INVENTION

Treatment options for varicose veins and telangiectasia (spider veins) include surgery, laser and radiofrequency ablation as well as sclerotherapy. Sclerotherapy relies on the effect of sclerosing agents, which induce sclerosis of blood vessels after injection via causing a fibrosis effect occluding the lumen of the vessel. This minimally invasive procedure offers an alternative to surgical interventions for managing venous insufficiency. Ultrasound-guided injection techniques are often employed to ensure precise delivery of the sclerosing agent. Treatment for leg varices and telangiectasia is often aimed at symptom relief or cosmetic improvement.

Polidocanol and sodium tetradecyl sulfate are established sclerosing agents for the treatment of varicose veins in the leg as well as reticular or spider veins. The agents are provided as sterile injectable solution (sclerosing solutions) and can also be administered as so-called microfoam.

Polidocanol is a polyethylene glycol ether of lauryl alcohol. The mean extent of polymerization (n) of the ethylene oxide units is approximately 9 resulting in an average molecular weight of approximately 582.8 g/mol. Synonym terms for polidocanol and product names include Aethoxysklerol (trademark, registered to CHEMISCHE FABRIK KREUSSLER & Co GMBH), Varithena (trademark, registered to BOSTON SCIENTIFIC MEDICAL DEVICE LIMITED), Asclera (trademark, registered to CHEMISCHE FABRIK KREUSSLER & Co GMBH), laureth 9, laureth-9, macrogol 9 lauryl ether, nonaethylene glycol monododecyl ether, nonaethylene glycol monolauryl ether, PEG-9 lauryl ether, polydocanol, polyethylene glycol 450 lauryl ether, polyoxyl 9 lauryl ether, lauromacrogol 400, and lauromacrogol 450. Polidocanol may be abbreviated as PDC.

Types of varicose veins, for which clinical efficacy of polidocanol treatment was demonstrated include uncomplicated spider veins (≤1 mm in diameter) and reticular veins (1-3 mm in diameter). Also, treatment of chronic venous insufficiency, in particular varicose great saphenous veins and advanced venous disease involving leg ulcers was studied with positive clinical outcomes.

Sodium tetradecyl sulfate is an anionic surfactant containing a sulfuric acid monoester functional group. It is indicated for the treatment of small uncomplicated varicose veins of the lower extremities that show simple dilation with competent valves. Sodium tetradecyl sulfate (STS) formulations are marketed as Sotradecol (trademark, registered to MYLAN PHARMA GROUP LIMITED), Trombovar (trademark, registered to KREUSSLER & CO PRODUITS CHIMIQUES) with concentrations of 1% or 3%.

One of the optical complications of sclerotherapy is hyperpigmentation in terms of brown marks and staining, which occurs following polidocanol administration in 10% to 30% of patients. This phenomenon is also referred to as post-sclerotherapy pigmentation.

Sclerotherapy benefits from the combination with duplex ultrasound for diagnostics, specific localization and imaging during the application. An additional improvement was related to establishing foam sclerotherapy, wherein the sclerosing agent is applied in the nature of a foam (Breu et al., 2008). The formulation of a foam with either air or carbon dioxide is considered to be more efficacious in causing sclerosis than the liquid formulation because the foam does not mix with the blood in the vessel and remains at the side of injection causing maximal sclerosant action. (Eckmann, 2009).

However, established formulations at least partially suffer from a wider variation in foam stability such that further optimization is desirable (Bai et al., 2020). Hyaluronic acid and Pluronic-F68 have been studied for their contribution in enhancement of foam stability for polidocanol (Del Castillo-Santaella et al., 2020). Other authors studied how additives such as tween, glycerin and xanthan gum affected the stability and rheological properties of polidocanol foam (Nastasa et al., 2015).

SHORT DESCRIPTION OF THE INVENTION

The present invention relates to a sclerosing agent for use in treating a varicose, reticular or spider vein, wherein the sclerosing agent is administered in a formulation further comprising a water-soluble cellulose derivative.

The invention provides a novel and improved therapeutic use of a sclerosing agent such as polidocanol or sodium tetradecyl sulfate in that it is administered in combination with a water-soluble cellulose derivative, i.e. in an aqueous formulation further comprising the cellulose derivative as excipient. For example, hydroxypropyl methylcellulose (HPMC), also known as hypromellose, is a well-characterized water-soluble cellulose derivative suitable as excipient in pharmaceutical and cosmetic formulations. The inventors surprisingly found that the effect of polidocanol in the context of sclerotherapy can be improved by administration in a combination with HPMC. When combined with HPMC, preliminary data indicate an improvement of the treatment efficacy and the aesthetic outcomes, for example in terms of reduction of undesired discoloration.

Accordingly, the present invention is suitable for use in a method for sclerotherapy of venous blood vessels. The invention concerns i) a sclerosing agent administered in a formulation further comprising a water-soluble cellulose derivative for (use in) the treatment of a varicose, reticular or spider vein, ii) a use of a sclerosing agent administered in a formulation further comprising a water-soluble cellulose derivative in the treatment of a varicose, reticular or spider vein, and/or iii) a use of a sclerosing agent in the manufacture of a medicament, in particular a medicament for treatment of a varicose, reticular or spider vein, said the medicament further comprising a water-soluble cellulose derivative.

The present invention relates to a method for sclerotherapy of venous blood vessels, preferably for the treatment of a varicose, reticular or spider vein in a subject in need thereof, wherein the method comprises administering a formulation, preferably in the form of a foam, preferably by direct injection into a varicose, reticular or spider vein or into the lumen of a trunk vein related to a varicose, reticular or spider vein to said vein, wherein said formulation comprises a sclerosing agent and a water-soluble cellulose derivative, e.g., polidocanol and hydroxypropyl methylcellulose, in an amount effective for inducing sclerosis of a varicose, reticular or spider vein.

Besides, the therapeutic and cosmetic uses or methods, the invention also provides a pharmaceutical composition comprising a sclerosing agent and a water-soluble cellulose derivative. As shown in the examples, the sclerosing agent polidocanol and the water-soluble cellulose derivative HPMC were formulated in a composition suitable for a pharmaceutical product. In particular, combined solutions comprising the sclerosing agent polidocanol and the water-soluble cellulose derivative HPMC are suitable starting material for producing a foam formulation with good stability over time and thus, they provide for an injectable formulation in the form of a foam generated from said combined solution or composition and a gas.

In other aspects, the invention relates to a kit for producing an injectable foam formulation and a method for producing an injectable foam formulation.

DETAILED DESCRIPTION OF THE INVENTION/PREFERRED EMBODIMENTS

In one aspect, the invention is defined as a sclerosing agent for use in treating a varicose, reticular or spider vein, wherein the sclerosing agent is administered in a formulation further comprising a water-soluble cellulose derivative. Hence, the invention relates to the specific medical use of a sclerosing agent administered in the defined formulation. The medical use and method of treatment according to the invention are characterized in that the sclerosing agent is administered in a formulation further comprising a water-soluble cellulose derivative.

In another aspect, the invention relates to a pharmaceutical composition comprising a sclerosing agent and a water-soluble cellulose derivative. Said composition is suitable as the formulation for use according to the invention and/or for producing or preparing the formulation for use according to the invention. Hence, the invention also relates to the pharmaceutical composition for (medical) use in treating a varicose, reticular or spider vein.

In a preferred embodiment, said formulation for use according to the invention and said pharmaceutical composition is for sclerotherapy. Accordingly, the formulation/composition is administered (or configured for being administered) via injection into a varicose, reticular or spider vein or into the lumen of a trunk vein related to a varicose, reticular or spider vein.

Preferably, the varicose, reticular or spider vein to be treated is a vein in a patient's extremity, preferably a leg. As to a varicose vein, it is particularly preferred that it is a (small) vein with outward visibility.

The sclerosing agent preferably is selected from the group of compounds suitable for sclerotherapy of reticular or spider veins as well as varicose veins in the leg, such as the group consisting of polidocanol and sodium tetradecyl sulfate. These sclerosing agents are established for sclerotherapy of reticular or spider veins as well as varicose veins in the leg. In contrast, the mild sclerosing agent ethanolamine oleate (trademark: Ethamolin) is limited to the treatment of patients with esophageal varices that have recently bled, to prevent rebleeding. Of note, in management of esophageal varices, cosmetic considerations play no role as the relevant veins have no outward visibility.

Cellulose derivatives are modified forms of cellulose, the primary structural component of plant cell walls. These derivatives are created by chemically altering the hydroxyl groups of the glucose units in cellulose, resulting in materials with diverse properties and applications. A cellulose derivative is considered to be water-soluble, if soluble in water with a concentration of at least 0.1 mg/mL, preferably at least 1 mg/mL, preferably at least 5 mg/mL. The skilled person will appreciate that factors such as temperature. pH and salt concentration influence solution behavior of water-soluble cellulose derivatives.

Many water-soluble cellulose derivatives are non-toxic. Non-toxic and water-soluble cellulose derivatives are widely used in pharmaceuticals, food, cosmetics, and other industries due to their safety and solubility in water. Hence, they are established as pharmaceutically acceptable excipients and applied as thickening agent, stabilizer, emulsifier of semi-solid and liquid formulations or film-forming agent and binder in solid formulations. Due to the gelling properties of the cellulose derivatives an aqueous solution comprising the same is typically characterized by a viscosity higher than that of the solvent without the cellulose derivative. Hence, herein, a solution thereof may also be referred to as hydrogel, without implying specific limitations as to its rheological properties.

Preferably, the water-soluble cellulose derivative is selected from the group of cellulose ethers, including non-ionic cellulose ethers such as methyl cellulose (MC), hydroxyethyl cellulose (HEC), hydroxypropyl cellulose (HPC), and hydroxypropyl methylcellulose (HPMC) as well as ionic cellulose ethers such as carboxymethylcellulose (CMC). The advantages of HPMC were demonstrated in the examples. Other listed water-soluble cellulose derivatives are available with similar properties regarding their viscosity and solubility and expected to have similar effects.

In a preferred embodiment, the water-soluble cellulose derivative is selected from the group consisting of methyl cellulose, hydroxyethyl cellulose, hydroxypropyl cellulose, hydroxypropyl methylcellulose, sodium carboxymethylcellulose, and mixtures thereof, preferably hydroxypropyl methylcellulose.

In a particularly preferred embodiment, the formulation for use according to the invention and the pharmaceutical composition comprise the sclerosing agent polidocanol and the water-soluble cellulose derivative hydroxypropyl methylcellulose.

In another preferred embodiment, the formulation for use according to the invention and the pharmaceutical composition is a sterile aqueous solution. Sterility is prerequisite for the safe use of a formulation in sclerotherapy. The term "sterile" as used herein is to be understood in accordance with the art specifying a composition/formulation complying with the microbiological standards as defined for cosmetic or pharmaceutical products, for example in the United States Pharmacopoeia (USP), the European Pharmacopoeia (Ph. Eur.) or other national standards. An aqueous composition/formulation comprising a water-soluble cellulose derivative may be sterilized after being filled into syringes, vials or ampoules. Thermal moist-heat sterilization with an autoclave is one of the standard methods, which comprises subjecting the compositions to high pressure saturated steam at 121° C. for around 15-20 minutes.

In a preferred embodiment, the pharmaceutical composition comprises the sclerosing agent, preferably polidocanol, in a concentration of from about 0.1% w/v to about 3.0% w/v, preferably from about 0.25% w/v to about 1.0% w/v, such as about 0.3, 0.4 or 0.5% w/v.

In a preferred embodiment, the pharmaceutical composition comprises the water-soluble cellulose derivative, preferably hydroxypropyl methylcellulose, in a concentration of from about 0.5% w/v to about 15% w/v, preferably from about 1.0% w/v to about 5.0% w/v, such as about 1.2, 1.3, 1.4, 1.5, 1.6, 1.7, 1.8, 1.9 or 2.0% w/v.

Besides the sclerosing agent and the water-soluble cellulose derivative, the main component of the composition is water, preferably water for injection. Possible further components include pharmaceutically acceptable excipients. According to the experimental results, pharmaceutically acceptable excipients are not necessary to obtain suitable compositions, but their addition should not be excluded. For example, the composition can include buffer salt(s) and co-solvent(s), in particular alcoholic co-solvents such as ethanol, benzyl alcohol or glycerol. Pharmaceutically acceptable excipients also include further pharmaceutically acceptable (water-soluble) polymers other than non-cellulose derivatives that are known to modulate viscosity and injectability, such as for example hyaluronic acid.

Exemplarily, the composition comprises (or consists of)
a sclerosing agent, preferably polidocanol, in a concentration of from about 0.1% w/v to about 3.0% w/v, preferably from about 0.25% w/v to about 1.0% w/v, such as about 0.3, 0.4 or 0.5% w/v,
a water-soluble cellulose derivative, preferably hydroxypropyl methylcellulose, in a concentration of from about 0.5% w/v to about 15% w/v, preferably from about 1.0% w/v to 5.0% w/v,
buffer salt(s) in a concentration of from 0% w/v to about 1.0% w/v,
alcoholic co-solvent(s), preferably ethanol, benzyl alcohol or glycerol, in a concentration of from 0% w/v to about 5.0% w/v, and
water.

A concentration range starting from a value of 0% w/v implies that this component is not included in the composition (0%) or is included therein (>0%). The concentrations in % w/v indicate the concentration ratio in terms of weight per volume and refer to the total volume of the composition. It is to be understood that the concentration ratios relate to the volume of the composition in its liquid form, i.e. without gaseous component.

The concentration values refer to a dilute aqueous solution with a density of approximately 1 g/cm$^3$. Accordingly, the concentration can be expressed interchangeably in either weight percent (w/w) or volume percent (w/v), as the values are nearly equivalent for these solutions.

In another preferred embodiment, said formulation for use according to the invention and the pharmaceutical composition is an injectable composition. Preferably, the formulation for use and composition are injectable in the form of a foam generated from the composition and a gas.

In a preferred embodiment, the pharmaceutical composition is a foam-forming composition, i.e. the composition allows for producing a foam formulation.

The invention further relates to a method and a kit for producing an injectable foam formulation.

The method for producing an injectable foam formulation comprises (the steps of)
providing a combined solution, wherein the combined solution is
(i) a sterile aqueous solution comprising a sclerosing agent and a water-soluble cellulose derivative, or
(ii) the result of combining a first sterile aqueous solution comprising a sclerosing agent and a second sterile aqueous solution comprising a water-soluble cellulose derivative,
mixing the combined solution with a gas to obtain a foam, preferably a defined amount of a gas.

The product of said method is a foam formulation comprising a sclerosing agent and a water-soluble cellulose derivative.

For example, in an embodiment of the providing step according to alternative (i) above, the sterile aqueous solution may be the pharmaceutical composition according to the invention. In an embodiment according to alternative (ii) above, the sclerosing agent and the water-soluble cellulose derivative are initially in two different solutions, i.e. a first and a second solution. In this embodiment, the method may further include a step of combining the two solutions under aseptic conditions. This embodiment allows to rely on an established (independent) product comprising a sclerosing agent, such as a commercially available medicinal product comprising either polidocanol or sodium tetradecyl sulfate.

The step of mixing the combined solution with a gas is performed under conditions suitable to result in a foam, wherein said gas is dispersed in the combined solution. The skilled person is familiar with conditions and steps suitable to obtain a foam. Exemplary techniques of foam formation in the context of sclerotherapy are for example referred to as Tessari Tourbillon Technique and variations thereof are exemplarily described by Witheley et al., 2015.

In a preferred embodiment, mixing is performed by using a set of containers, e.g. at least two syringes, and at least one connector. For example, when using the double-syringe system technique for foam formation two Luer Lock syringes are connected with a Luer-to-Luer adapter to mix the combined solution with a gas via transfer between the syringes. As shown in the examples, the simple mechanical treatment is sufficient to disperse a gas like air within the aqueous composition comprising a sclerosant agent and a water-soluble cellulose derivative and allows for formation of a foam. Exemplarily, the connector may also be provided in form of a three-way stopcock with suitable connection points to syringes or as a bi-directional check-valve.

A suitable gas for the method according to the invention may be selected from the group consisting of air, carbon dioxide, oxygen and mixtures thereof, such as a mixture of carbon dioxide and oxygen. In a preferred embodiment, the gas is purified or sterile, i.e. excluding ambient air.

In a preferred embodiment, the method is comprising transferring the foam in a syringe for injection. This step is preferably the final step of the method, as it results in a formulation ready to be applied in the medical use according to the present invention.

The kit for producing an injectable foam formulation comprises a set of containers, preferably syringes, configured for producing a foam, instructions for producing an injectable foam, and
(i) a sterile aqueous solution comprising a sclerosing agent and water-soluble cellulose derivative,
(ii) a first sterile aqueous solution comprising a sclerosing agent and a second sterile aqueous solution comprising a water-soluble cellulose derivative, or
(iii) a sterile aqueous solution comprising a water-soluble cellulose derivative configured for combination with an aqueous solution comprising a sclerosing agent.

For example, in an embodiment according to alternative (i) above, the sterile aqueous solution may be the pharmaceutical composition according to the invention.

In an embodiment according to alternative (ii) above, the sclerosing agent and the water-soluble cellulose derivative are provided as part of the kit in two different solutions, i.e. first and second solution. In this embodiment, the instructions for producing an injectable foam preferably also include an instruction for combining the two solutions under aseptic conditions.

In an embodiment according to alternative (iii) above, the sclerosing agent is not part of the kit. However, the sterile aqueous solution comprising a water-soluble cellulose derivative is configured such that it is readily combinable with an aqueous solution comprising a sclerosing agent, i.e. an independent product comprising the sclerosing agent, such as a commercially available product comprising either polidocanol or sodium tetradecyl sulfate. In this embodiment, the instructions for producing an injectable foam preferably also include an instruction for combining the two solutions under aseptic conditions.

The preferred embodiments of the pharmaceutical composition according to the invention analogously apply for the solution(s) provided as part of the kit according to the embodiment (ii) or (iii), and the skilled person understands how to transfer the preferences to the latter solution(s).

In a preferred embodiment, the containers are pre-filled with the sterile solution(s) according to an embodiment (i) to (iii) and/or a defined amount of gas, such as sterile air.

The instructions for producing an injectable foam preferably include operating orders for performing a method for producing a foam, preferably the method for producing an injectable foam formulation according to the invention as described above. For example, the instructions for use may reflect aspects of foam stability over time and include appropriate timelines and/or operating measures (e.g. repeating foaming steps) to ensure a good foam quality for use.

It is further preferred, that the kit comprises instructions for administering the injectable foam formulation, and preferably a needle for injection.

BRIEF DESCRIPTION OF THE DRAWINGS

The foregoing and other objects, features and advantages of the invention will become more apparent from the following figures and non-limiting examples.

EXAMPLES

Figure 1:
FIG. 1 shows a photograph of a vial containing a composition with polidocanol and HPMC (1.6HPMC/0.3PDC).

Example 1: Preparation of Sterile Solutions Comprising HPMC

Four solutions with HPMC in concentrations of 1.5% (m/m), 2% (m/m), 2.4% (m/m) and 3% (m/m) were prepared.

To prepare a 1.5% HPMC solution, 1.524 g HPMC (Methocel E4M Premium, loss on drying 1.6%, apparent viscosity 3800 mPas) were dissolved in a beaker in 98.935 g hot phosphate buffer comprising NaCl under stirring for about 20 minutes using an anchor stirrer (150 rpm). For cooling, the beaker was placed in a cold-water bath and the hydrogel was stirred for another 40 minutes. Water for injection (WFI) was then added to a final weight of the hydrogel of 100.456 g, followed by stirring for 10 minutes at 100 rpm and room temperature.

To prepare a 2% HPMC solution, 2.032 g HPMC (Methocel E4M Premium, loss on drying 1.6%, apparent viscosity 3800 mPas) were dissolved in a beaker in 98.944 g hot phosphate buffer comprising NaCl under stirring for about 20 minutes using an anchor stirrer (150 rpm). For cooling, the beaker was placed in a cold-water bath and the hydrogel was stirred for another 40 minutes. Water for injection (WFI) was then added to a final weight of the hydrogel of 100.976 g, followed by stirring for 10 minutes at 100 rpm and room temperature.

To prepare a 2.4% HPMC solution, 2.439 g HPMC (Methocel E4M Premium, loss on drying 1.6%, apparent viscosity 3800 mPas) were dissolved in a beaker in 97.604 g hot phosphate buffer comprising NaCl under stirring for about 20 minutes using an anchor stirrer (150 rpm). For cooling, the beaker was placed in a cold-water bath and the hydrogel was stirred for another 40 minutes. Water for injection (WFI) was then added to a final weight of the hydrogel of 100.077 g, followed by stirring for 10 minutes at 100 rpm and room temperature.

To prepare a 3% HPMC solution, 3.048 g HPMC (Methocel E4M Premium, loss on drying 1.6%, apparent viscosity 3800 mPas) were dissolved in a beaker in 97.601 g hot phosphate buffer comprising NaCl under stirring for about 20 minutes using an anchor stirrer (150 rpm). For cooling, the beaker was placed in a cold-water bath and the hydrogel was stirred for another 40 minutes. Water for injection (WFI) was then added to a final weight of the hydrogel of 100.654 g, followed by stirring for 10 minutes at 100 rpm and room temperature.

Clear glass injection vials (filling volume 10 mL) with septum caps and aluminium septum closure caps containing 5 g of each solution were prepared and autoclaved at 121° C. for 15 min.

Example 2 Rheological Characterization of a Sterile Solutions Comprising HPMC Rheological characterization was performed of sterile HPMC solutions comprising 2.0% and 2.4% of HPMC, respectively. Rheological measurements were performed in triplicate using an Anton Paar MCR 102 Rheometer with a cone-plate system. The dynamic viscosity was measured at a constant shear rate of 5/s and at a temperature of 25° C. The mean dynamic viscosity was 2725 mPas and 4662 mPas, for the 2.0% and 2.4% HPMC solutions, respectively.

Example 3: Preparation of Combined Solutions with Aethoxysklerol 2%

Four different combined solutions were prepared by via combining a sterile aqueous solution comprising Polidocanol at a concentration of 2% and a sterile aqueous solution comprising HPMC. The commercially available medicinal product Aethoxysklerol® 2% (Chem. Fabrik Kreussler & Co. GmbH: comprising 2% polidocanol) was added to the vials containing sterile solutions comprising HPMC in different concentrations as prepared according to example 1. Homogenisation was achieved via slight manual agitation of the vials. The final concentrations of both HMPC and polidocanol (PDC) are summarized in Table 1, wherein for example 1.1HPMC/0.5PDC refers to a solution with a HPMC concentration of 1.1% and a concentration of polidocanol of 0.5%. The concentration of in all combined solutions was 0.5%.

TABLE 1

| | Preparation of combined solutions with Aethoxysklerol 2% | | |
|---|---|---|---|
| Combined solution | Initial HPMC concentration (%) | Initial amount of solution per vial (g) | Added volume of Aethoxysklerol 2% (mL) |
| 1.1 HPMC/0.5 PDC | 1.5 | 5 | 1.67 |
| 1.5 HPMC/0.5 PDC | 2 | 5 | 1.67 |

TABLE 1-continued

| | | | |
|---|---|---|---|
| Preparation of combined solutions with Aethoxysklerol 2% | | | |
| Combined solution | Initial HPMC concentration (%) | Initial amount of solution per vial (g) | Added volume of Aethoxysklerol 2% (mL) |
| 1.8 HPMC/0.5 PDC | 2.4 | 5 | 1.67 |
| 2.2 HPMC/0.5 PDC | 3 | 5 | 1.67 |

Example 4: Preparation of Combined Solutions with Aethoxysklerol 3%

Four different combined solutions were prepared via combining a sterile aqueous solution comprising Polidocanol at a concentration of 2% and a sterile aqueous solution comprising HPMC. The commercially available medicinal product Aethoxysklerol 3% was added to sterile solutions comprising HPMC in different concentrations. Homogenisation was achieved via slight manual agitation of the vials. The preparation and final concentrations of HMPC and polidocanol (PDC) are indicated in Table 2. The final concentration of polidocanol in all combined solutions was 0.5%.

TABLE 2

| | | | |
|---|---|---|---|
| Preparation of combined solutions with Aethoxysklerol 3% | | | |
| Combined solution | Initial HPMC concentration (%) | Initial amount of solution per vial (g) | Added volume of Aethoxysklerol 3% (mL) |
| 1.3 HPMC/0.5 PDC | 1.5 | 5 | 1 |
| 1.7 HPMC/0.5 PDC | 2 | 5 | 1 |
| 2.0 HPMC/0.5 PDC | 2.4 | 5 | 1 |
| 2.5 HPMC/0.5 PDC | 3 | 5 | 1 |

Example 5: Preparation of Combined Solutions with Aethoxysklerol 1%

A combined solution was prepared via combining a sterile aqueous solution comprising Polidocanol at a concentration of 1% and a sterile aqueous solution comprising HPMC. An amount of 2 mL of the commercially available product Aethoxysklerol 1% was added to 4 g of a sterile solution comprising 2.4% HPMC. The resulting combined solution 1.6HPMC/0.33PDC has a final HPMC concentration of 1.6% and a final polidocanol concentration of 0.33%. A vial filed with the clear resulting solution is shown in FIG. 1.

Table 3 summarizes said example plus further preparations starting with a sterile solution comprising 2.4% HPMC and the commercially available product Aethoxysklerol 1%. The final concentrations of HPMC and polidocanol (PDC) in the combined solution are indicated. After combining the sterile solution comprising HPMC with the commercially available product Aethoxysklerol 1% the final volumes range from 6 to 10 mL per vial.

TABLE 3

| | | | |
|---|---|---|---|
| Preparation of combined solution with Aethoxysklerol 1% | | | |
| Combined solution | Initial HPMC concentration (%) | Initial amount of solution per vial (g) | Added volume of Aethoxysklerol 1% (mL) |
| 1.6 HPMC/0.33 PDC | 2.4 | 4 | 2 |
| 1.2 HPMC/0.50 PDC | 2.4 | 4 | 4 |
| 1.3 HPMC/0.44 PDC | 2.4 | 5 | 4 |
| 1.4 HPMC/0.40 PDC | 2.4 | 6 | 4 |

Example 6: Osmolality and pH of Combined Solutions

Combined solutions comprising a sclerosing agent (Polidocanol) and a water-soluble cellulose derivative (HPMC) were characterized regarding their osmolality and pH, i.e. characteristics crucial for their suitability for medical or cosmetical purposes. Osmolality and pH of combined solutions prepared as described in Examples 3, 4 and 5 were determined in triplicate prior to foam formation (see Table 4). Based on these properties, the combined solutions are suitable as pharmaceutical composition for injection.

TABLE 4

| | | |
|---|---|---|
| Osmolality and pH of combined solutions | | |
| Combined solution | Osmolality (mOsmol/kg) | pH |
| 1.5 HPMC/0.5 PDC | 445 | 7.2 |
| 1.6 HPMC/0.3 PDC | 504 | 7.3 |
| 1.7 HPMC/0.5 PDC | 392 | 7.2 |
| 1.8 HPMC/0.5 PDC | 447 | 7.2 |
| 2.0 HPMC/0.5 PDC | 390 | 7.2 |

The following mean osmolality values were obtained for the commercially available medicinal products Aethoxysklerol 2% and Aethoxysklerol 3%, which were used for the preparation of combined solutions as described in examples 3 and 4:964 mOsmol/kg and 975 mOsmol/kg, respectively.

Example 7: Rheological Characterization of a Combined Solution

Combined solutions comprising a sclerosing agent (Polidocanol) and a water-soluble cellulose derivative (HPMC) were characterized regarding their rheological properties, in particular their dynamic viscosity. The rheological measurement was performed using an Anton Paar MCR 102 Rheometer with a cone-plate system. The dynamic viscosity was measured at a constant shear rate of 5/s and at a temperature of 25° C. The dynamic viscosity of the combined solution 1.6HPMC/0.3PDC prepared as described in example 5 was 1120 mPas.

Example 8: Preparation of Injectable Foam Formulations

For the formation of a foam, 3 mL of a combined solution comprising both polidocanol and HPMC were removed from the vial using a 3 mL syringe equipped with a 21G needle. The 3 mL syringe was connected to a second syringe containing about 1-2 mL air with a syringe connector, and the formulation was moved manually back and forth between the 2 syringes until a foam had formed (about 30 sec).

Directly after mixing, the formulations in the syringe appeared completely white and opaque, indicating that a foam had formed. All combined solutions allowed preparing a foam with good quality based on visual inspection. Visual inspection includes criteria like increase of volume compared to the combined solution, number and size of bubbles, lack of transparency (opacity).

Figure 2:
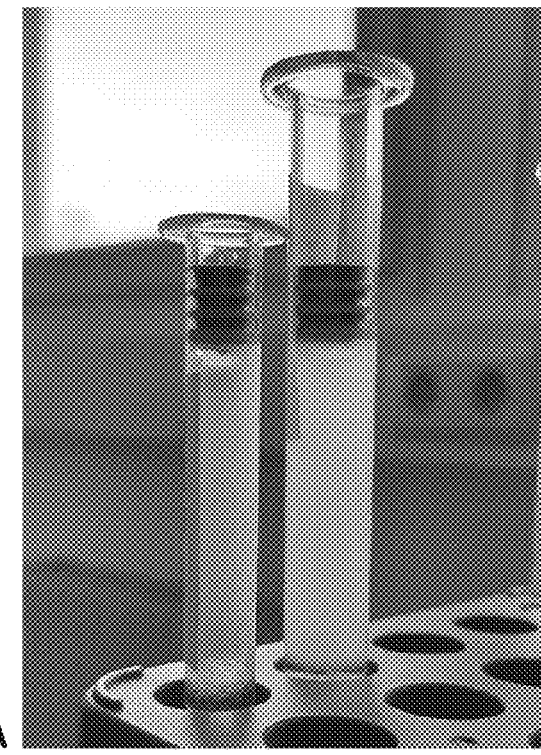
FIG. 2 shows photographs of syringes with a foam formulation prepared from of 1.8HPMC/0.5PDC (A) and 1.3HPMC/0.5PDC (B) 30 min after foam formation
Figure 2:
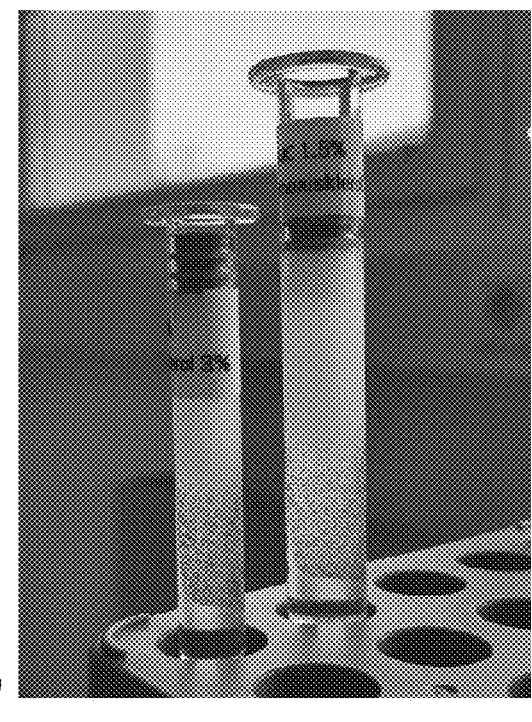

The stability of the foam was monitored for 30 min. If the formulation was still white and opaque the stability of the foam was classified as "good" (see FIG. 2A with 1.8HPMC/0.5PDC). If the formulation had then mostly reverted back to being clear with only a few air bubbles, the stability of the foam was qualified as "poor" (see FIG. 2B with 1.1HPMC/0.5PDC). The qualitative results are listed in Table 5. The stability of the foam positively correlated with the concentration of HPMC in the formulations.

TABLE 5

| Foam formation after mixing of combined solutions with air | | |
|---|---|---|
| Combined solution | Initial foam formation | Foam stability after 30 min |
| 1.1 HPMC/0.5 PDC | good | poor |
| 1.3 HPMC/0.5 PDC | good | poor |
| 1.5 HPMC/0.5 PDC | good | good |
| 1.7 HPMC/0.5 PDC | good | good |
| 1.8 HPMC/0.5 PDC | good | good |
| 2.0 HPMC/0.5 PDC | good | good |
| 2.2 HPMC/0.5 PDC | good | good |
| 2.5 HPMC/0.5 PDC | good | good |

Example 9: Extrusion Force of Injectable Foam Formulations

The injectability of foam formulations comprising both polidocanol and HPMC was determined directly after foam formation (the foam formulation being generated/prepared with the method as described in Example 8).

Foam was filled in glass syringes with a volume of either 3 mL or 1 mL, which were equipped with 34 G×8 mm needles. The extrusion force was measured with a Mecmesin force testing system and an extrusion rate of 12 mm/min. Measurements were performed in duplicate. The calculated mean extrusion force (EF) for each tested foam formulation is listed in Table 6. As expected, the extrusion force is higher when using a 3 mL syringe with a larger diameter in comparison to a 1 ml syringe. When using a 1 ml syringe and a 34 G needle the extrusion force of the foam formulations was mostly acceptable. The combined solution 2.5HPMC/0.5PDC with the highest HPMC concentration tested in this set-up for foam formation resulted in the highest ejection forces (EF>50 N).

Extrusion force measurements were also performed about 30 min after foam formation using 1 mL glass syringes and 34G needles with selected formulations. Single measurements were performed, and the results indicate that the extrusion force remained in an acceptable range 30 min after foam formation.

TABLE 6

| Extrusion force (EF) of injectable foam formulations | | | |
|---|---|---|---|
| Combined solution for | EF (N) initially after foam formation | | EF (N) 30 min after foam formation |
| foam preparation | 3 mL syringe | 1 mL syringe | 1 mL syringe |
| 1.1 HPMC/0.5 PDC | 43 | 17 | n.d. |
| 1.3 HPMC/0.5 PDC | 51 | 18 | n.d. |
| 1.5 HPMC/0.5 PDC | 61 | 26 | 26 |
| 1.7 HPMC/0.5 PDC | 71 | 43 | 30 |
| 1.8 HPMC/0.5 PDC | 87 | 27 | 32 |
| 2.0 HPMC/0.5 PDC | 84 | 38 | 34 |
| 2.2 HPMC/0.5 PDC | 98 | 43 | n.d. |
| 2.5 HPMC/0.5 PDC | 140 | 61 | n.d. |

Example 10: Stability of Polidocanol During Autoclavation

Polidocanol (Thesit, Gatt Koller GmbH) was analyzed before and after autoclavation (121° C./20 min) using the NMR method described in the European Pharmacopeia for determining the average chain length of the fatty alcohol and average number of moles of ethylene oxide. Test solutions were prepared by gently heating the sample and solving in a mixture of deuterated methanol and deuterated chloroform, which contained Chromium (III) acetylacetonate as a relaxation aid.

NMR spectra were recorded using an NMR spectrometer operating at minimum 300 MHz (Bruker Avance II 400 (N2 Kryo) (Prodigy) 400 MHz).

Figure 3:
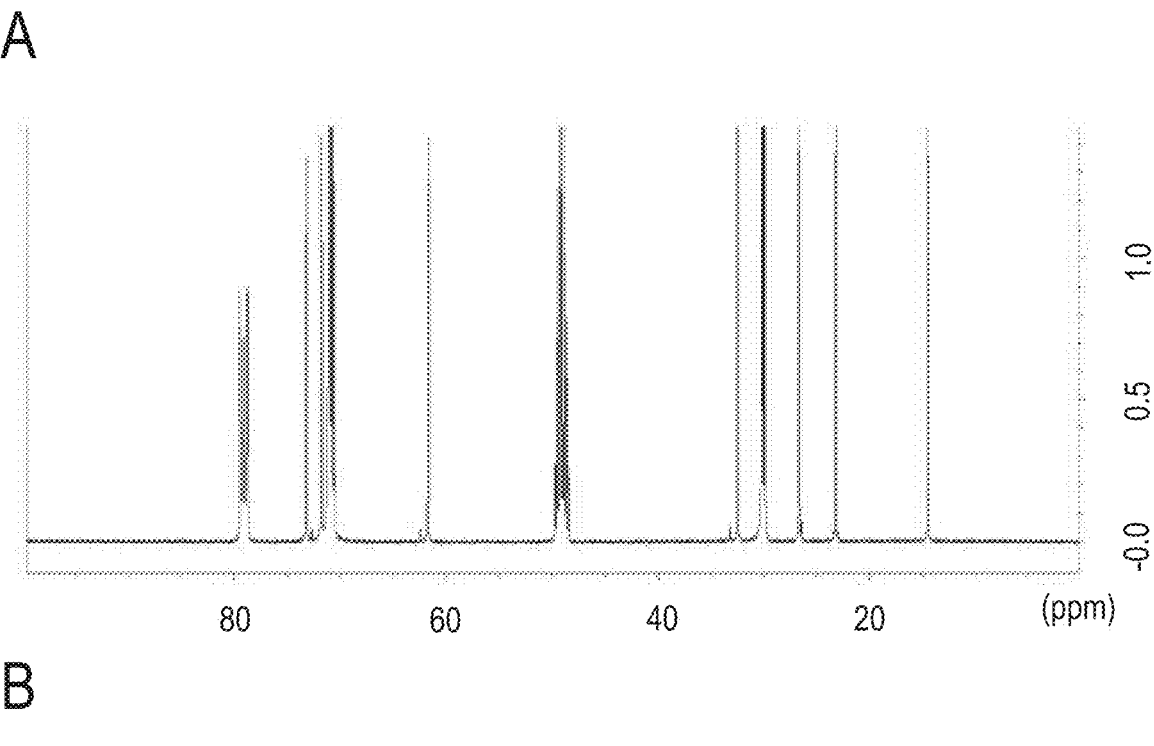
FIG. 3 shows 13C-NMR spectra for of polidocanol before (A) and after (B) autoclavation.
Figure 3:
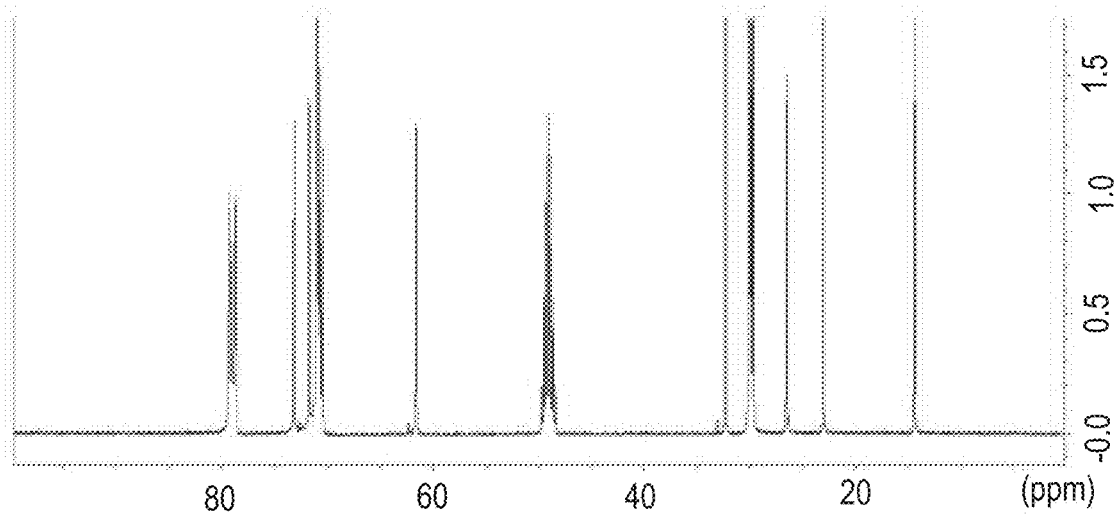

The 13C-NMR spectra resulting for the compound are shown in FIG. 3. No differences in the obtained 13-C-NMR profiles were detected, indicating that polidocanol seems to be stable during autoclavation.

Example 11: Clinical Evaluation

Clinical experience from individual case studies is summarized herein below:

a) Preparation of Composition and Injectable Foam

To 6 mL of a 2.4% HPMC solution 4 mL of an Aethoxysklerol® 1% solution (Chem. Fabrik Kreussler & Co. GmbH) are added in a 10 mL vial, mixed and drawn into a 20 mL syringe. The syringe filled with the combined solution is connected via a three-way stopcock to a second 20 ml syringe filled with 5 mL of air. By moving the air and the combined solution back and forth (approx. 20 times), a stable white foam formulation is formed in the two syringes.

b) Administration

The foam formulation is retrieved from the larger syringes via a 1 mL small-diameter syringe (e.g., an insulin syringe) and administered strictly intravascularly into the vessels to be sclerosed using an injection needle with a small diameter (e.g., a 34 G needle).

c) Observations Related to a First Treatment Session

Phase 1—the First 5 Minutes after Treatment:

The intravascular administration of the foam formulation displaces the blood in the vessels and the vessels are no longer visible due to the presence of the foam in the vessel. As a result of rapid edema formation in the vessel wall and in the adjacent tissue, a light pink and homogeneous thickening of the skin is observed in the entire injection area. This, and the formation of wheals over the injection sites are a sign of the clinical efficacy of the sclerosing agent. In contrast to the well-known foam therapy with Polidocanol alone (Aethoxysklerol®), no puncture bleeding and/or intravascular thrombus formation is observed.

Phase 2—Hours and Days after Treatment:

Any wheals and redness of the skin usually disappear within about 6 hours after administration. The treated vessels have either disappeared or, depending on their resilience, may become partially visible again. Depending on the damage that has occurred to the treated vessels, their contours begin to dissolve, and hence, the vessels may appear wider. The treated area of the skin can appear bluish and patchy.

Phase 3—Four Weeks after Treatment:

The treated blood vessels are barely visible.

d) Optional Second Treatment Session

Any remaining, still visible (i.e. perfused) vessels, which are usually bluish in color, are treated with the foam formulation as described above. The clinical observations immediately and up to a couple of hours after administration are the same as described above.

Final Phase—Three to Four Weeks after the Second Treatment:

The treated vessels have completely disappeared and the skin in the treated areas appears normal and healthy. No hyperpigmentation in terms of brown marks and staining is visible.

Example 12: Preparation of a Sterile Pharmaceutical Composition Comprising a Sclerosing Agent and a Water-Soluble Cellulose Derivative First, a solution comprising 2% (w/w) HPMC was prepared. In a beaker 10.1626 g of HPMC (Methocel E4 Premium, loss on drying 1.6%, apparent viscosity 3800 mPas) were dissolved in 450 g of hot water for injection by stirring with an anchor stirrer at 400 rpm for about 20 minutes. For cooling, the beaker was placed in a cold-water bath and the hydrogel was stirred for another 40 minutes. Water for injection (WFI) was then added to give a final weight of the hydrogel of 500 g. The hydrogel was stored at 2-8° C. until further use.

Polidocanol was gently heated to a temperature of about 40° C. To 0.5 g of polidocanol 4.5 g of WFI were added and the solution was kept for about 30 minutes at 40° C. After a brief homogenisation via vortexing the diluted polidocanol solution was added to 85.5 g of the solution comprising 2% HPMC. The resulting composition (comprising 0.5% polidocanol and 1.9% HPMC) was stirred with an anchor stirrer at room temperature for about 60 minutes. Then, 10 mL clear glass injection vials with septum caps and aluminium septum closure caps containing 5 g of the composition were prepared and autoclaved at 121° C. for 20 min. After cooling, the resulting composition presented as clear hydrogel.

Example 13: Rheological Characterization of a Pharmaceutical Composition Comprising Polidocanol and HPMC Rheological measurements were performed using an Anton Paar MCR 102 Rheometer with a cone-plate system. A flow curve was generated with a shear rate range from 0.01/s-1000/s. At shear rate 5/s the mean dynamic viscosity of the composition prepared according to Example 12 was 1600 mPas (n=6).

Example 14: Preparation of Injectable Foam Formulations

The pharmaceutical composition prepared as described in Example 12 was used to prepare a foam formulation. About 3 mL sterile composition were transferred from the vial into a 3 mL glass syringe. The 3 mL syringe was connected to a second syringe containing about 1 mL air with a syringe connector, and the formulation was moved manually back and forth between the 2 syringes until a foam had formed (about 30 sec).

Directly after mixing, the foam formulation in the syringe appeared completely white and opaque, indicating that a foam had formed. The pharmaceutical composition allowed preparing a foam with good quality based on visual inspection of criteria like increase of volume compared to the composition, and the number and size of bubbles. The stability of the foam was monitored for 15 min. After this time period the foam formulation appeared mostly clear with only a few air bubbles.

REFERENCES

Bai T, Liu Y, Jiang W, Li Y, Liu J, Yu C, Fan Y. A Review of Sclerosing Foam Stability in the Treatment of Varicose Veins. Dermatol Surg. 2020; 46(2):249-257

Breu F X, Guggenbichler S, Wollmann J C. Duplex ultrasound and efficacy criteria in foam sclerotherapy from the 2nd European Consensus Meeting on Foam Sclerotherapy 2006, Tegernsee, Germany. VASA. 2008; 37(1):90-95

Del Castillo-Santaella T, Yang Y, Martínez-González I, Gálvez-Ruiz M J, Cabrerizo-Vilchez MÁ, Holgado-Terriza J A, Selles-Galiana F, Maldonado-Valderrama J. Effect of Hyaluronic Acid and Pluronic-F68 on the Surface Properties of Foam as a Delivery System for Polidocanol in Sclerotherapy. Pharmaceutics. 2020; 12(11):1039

Eckmann D M. Polidocanol for endovenous microfoam sclerosant therapy. Expert Opin Investig Drugs. 2009; 18(12):1919-27

Nastasa V, Samaras K, Ampatzidis Ch, Karapantsios T D, Trelles M A, Moreno-Moraga J, Smarandache A, Pascu M L. Properties of polidocanol foam in view of its use in sclerotherapy. Int J Pharm. 2015; 478(2):588-96

Whiteley M S, Patel S B. Modified Tessari Tourbillon technique for making foam sclerotherapy with silicone-free syringes. Phlebology. 2015 October; 30(9):614-7. doi: 10.1177/0268355514554476. Epub 2014 Oct. 6. PMID: 25288590.

The invention claimed is:

1. A pharmaceutical composition comprising:

a sclerosing agent; and a water-soluble cellulose derivative, wherein the sclerosing agent is polidocanol, wherein the sclerosing agent is included at a concentration of about 0.1% (w/v) to about 1.0% (w/v), and the water-soluble cellulose derivative is included at a concentration of greater than 1.3% (w/v).

2. The pharmaceutical composition of claim 1, wherein the water-soluble cellulose derivative is selected from the group consisting of methyl cellulose, hydroxyethyl cellulose, hydroxypropyl cellulose, hydroxypropyl methyl cellulose, and sodium carboxymethylcellulose.

3. The pharmaceutical composition of claim 1, wherein the composition is a sterile aqueous solution.

4. The pharmaceutical composition of claim 1, wherein the composition comprises the sclerosing agent in a concentration of from about 0.25% (w/v) to about 1.0% (w/v).

5. The pharmaceutical composition of claim 1, wherein the composition comprises the water-soluble cellulose derivative in a concentration lower than 2.5% (w/v).

6. The pharmaceutical composition of claim 5, wherein the water-soluble cellulose derivative comprises hydroxypropyl methylcellulose.

7. The pharmaceutical composition of claim 1, wherein the water-soluble cellulose derivative comprises hydroxypropyl methylcellulose.

8. The pharmaceutical composition of claim 1, wherein the water-soluble cellulose derivative comprises hydroxypropyl methylcellulose and wherein the water-soluble cellulose derivative is included at a concentration lower than 2.5% (w/v).

9. A pharmaceutical composition comprising:

a sclerosing agent; and a water-soluble cellulose derivative, wherein the sclerosing agent is polidocanol, and the sclerosing agent is hydroxypropyl methylcellulose, wherein the sclerosing agent is included at a concentration of from about 0.1% (w/v) to about 1.0% (w/v), wherein the water-soluble cellulose derivative is included at a concentration of greater than 1.3% (w/v) and lower than 2.5% (w/v), and wherein the composition is a sterile aqueous solution.

* * * * *